United States Patent
Harris et al.

(10) Patent No.: US 10,421,738 B2
(45) Date of Patent: Sep. 24, 2019

(54) CHIRAL CYCLODECYNES AND METHODS

(71) Applicant: Florida State University Research Foundation, Inc., Tallahassee, FL (US)

(72) Inventors: Trevor Michael Harris, Tallahassee, FL (US); Igor V. Alabugin, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 16/017,106

(22) Filed: Jun. 25, 2018

(65) Prior Publication Data

US 2018/0370943 A1    Dec. 27, 2018

Related U.S. Application Data

(60) Provisional application No. 62/524,743, filed on Jun. 26, 2017.

(51) Int. Cl.
| | | |
|---|---|---|
| *C07D 321/00* | (2006.01) | |
| *C07D 245/04* | (2006.01) | |
| *C07B 43/04* | (2006.01) | |
| *C07B 41/04* | (2006.01) | |

(52) U.S. Cl.
CPC .......... *C07D 321/00* (2013.01); *C07B 41/04* (2013.01); *C07B 43/04* (2013.01); *C07D 245/04* (2013.01); *C07B 2200/07* (2013.01)

(58) Field of Classification Search
CPC .............................. C07D 321/00; C07D 245/04
USPC ...................................................... 540/471
See application file for complete search history.

(56) References Cited

PUBLICATIONS

Koch-Pomeranz et al., Helvetica Chimica Acta (1973), 56(8), 2981-3004.*
Agard et al., "A Strain-Promoted [3+2] Azide-Alkyne Cycloaddition for Covalent Modification of Biomolecules in Living Systems," J. Am. Chem. Soc., 2004, 126:15046-15047.
Baskin et al., "Copper-Free Click Chemistry for Dynamic in vivo Imaging," PNAS, 2007, 104(43):16793-16797.
Gold et al., "Moderating Strain without Sacrificing Reactivity: Design of Fast and Tunable Noncatalyzed Alkyne-Azide Cycloadditions via Stereoelectronically Controlled Transition State Stabilization," J. Am. Chem. Soc., 2013, 135:1558-1569.
Hagendorn et al., "A New Route to Dithia- and Thiaoxacyclooctynes via Nicholas Reaction," RSC Adv., 2014, 15493-15495.
Kaneda et al., "2-Aminobenzenesulfonamide-Containing Cyclononyne as Adjustable Click Reagent for Strain-Promoted Azide-Alkyne Cycloaddition," Org. Lett., 2017, 19:1096-1099.
Kolb et al., "Click Chemistry: Diverse Chemical Function from a Few Good Reactions," Angew. Chem. Int. Ed., 2001, 40:2004-2021.
Ni et al., "Heteroatom-Embedded Medium-Sized Cycloalkynes: Concise Synthesis, Structural Analysis, and Reactions," Angew. Chem. Int. Ed., 2015, 54:1190-1194.
Thirumurugan et al., "Click Chemistry for Drug Development and Diverse Chemical-Biology Applications," Chem. Rev., 2013, 113:4905-4979.

\* cited by examiner

*Primary Examiner* — Niloofar Rahmani
(74) *Attorney, Agent, or Firm* — Eversheds Sutherland (US) LLP

(57) ABSTRACT

Provided herein are cyclodecynes, including chiral cyclodecynes, and methods of making cyclodecynes. The methods may include providing a 1,1'-biaryl compound substituted independently at the 2-position and the 2'-position with a hydroxyl or an amino group; and contacting the 1,1'-biaryl compound with a protected but-2-yne-1,4-diol to form the cyclodecyne.

9 Claims, 10 Drawing Sheets

CHIRAL CYCLODECYNES AND METHODS

CROSS-REFERENCE TO RELATED APPLICATIONS

This application claims priority to U.S. Provisional Patent Application No. 62/524,743, filed Jun. 26, 2017, which is incorporated herein by reference.

BACKGROUND

Click chemistry has the potential to achieve functional group orthogonality, high yields, and/or other advantages in diverse applications, ranging from surface functionalization to drug delivery. However, the utility of a prototypical click reaction, the Cu-catalyzed alkyne-azide cycloaddition, can be hampered by the toxicity of copper salts towards living systems, their deleterious effects on redox-sensitive nanoparticles, or a combination thereof.

Strain-promoted alkyne-azide cycloaddition has been shown to address one or more of these limitations in bioorthogonal chemistry and surface chemistry. However, strain-activated cycloalkynes typically balance at the edge of instability, which can complicate synthesis and/or applications of such reactive molecules.

A ~50-fold increase in reactivity of a difluorinated cyclooctyne (DIFO) relative to the parent cyclooctyne has been reported, which indicated that one or more other factors may be harnessed to supplement strain activation (Baskin, J. M. et al., *Proc. Natl. Acad. Sci. U.S.A.* 104, 16793 (2007)). It also has been reported that an endocyclic oxygen and nitrogen can be comparable in reactivity to DIFO (Ni, R. et al., *Angew. Chem. Int. Ed.* 54, 1190 (2015)).

Generally, the structural design of cycloalkynes in click chemistry include alkyne bending, sometimes amplified by one or more other external factors, such as ion sensing. Assembly of a cyclodecyne frame typically involves nucleophilic substitutions. The direct nucleophilic substitution approach to make smaller cycloalkynes usually is difficult due to the entropic and/or enthalpic penalty for the formation of strained rings. Previous success of cyclononyne synthesis has relied heavily on the Nicholas reaction to assemble the ring, an approach that requires two additional steps to protect and deprotect the alkyne (Ni, R. et al., *Angew. Chem. Int. Ed.* 54, 1190 (2015); and Kaneda, K. et al., *Org. Lett.* 19, 1096 (2017)).

Methods, including relatively facile methods, are desired that may introduce twisting along a cycloalkyne backbone that starts from the alkyne and passes through endocyclic C—X bonds to a biaryl core. Also desired are methods that demonstrate that the electronic energy stored in the twisted structure can be harvested in the click cycloaddition transition state (TS), and/or are capable of having a biaryl moiety introduce axial chirality due at least in part to the fact that restricted bond rotation may create atropisomers.

BRIEF SUMMARY

Provided herein are methods and compounds that may address one or more of the foregoing needs. In some embodiments, chiral cyclodecynes and methods of making chiral cyclodecynes are provided, and the chiral cyclodecynes may be prepared on at least a gram scale, prepared in an enantiopure form, purified by recrystallization, or a combination thereof. Not wishing to be bound by any particular theory, it is believed that embodiments of the cyclodecynes provided herein can be more reactive towards azides than activated cyclononynes, and may approach the reactivity of cyclooctynes.

Methods of making cyclodecynes are provided. In some embodiments, the methods include providing a 1,1'-biaryl compound substituted independently at the 2-position and the 2'-position with a hydroxyl or an amino group; and contacting the 1,1'-biaryl compound with a protected but-2-yne-1,4-diol to form the cyclodecyne.

Also provided herein are cyclodecynes.

DETAILED DESCRIPTION

Figure 1:
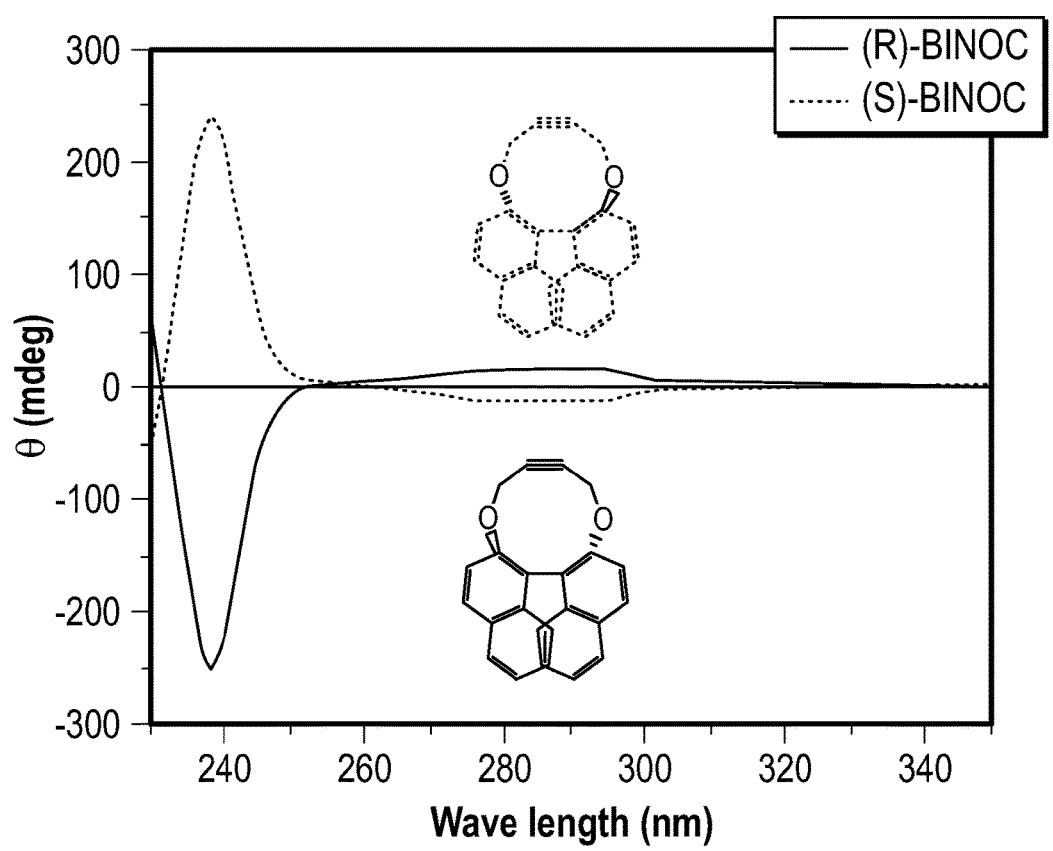
FIG. 1 depicts the overlap of circular dichroism spectra for (R) and (S) enantiomers of an embodiment of a cyclodecyne.

Provided herein are cyclodecynes and methods of making cyclodecynes. Embodiments of the cyclodecynes and methods provided herein may add axial chirality to the click chemistry toolbox. The "twisted and bent" cyclodecyne structural motif of some embodiments described herein may be intertwined with dormant electronic effects to potentially open a conceptually new way to control click reactivity. Although endocyclic heteroatoms can provide dual stabilization to the cycloalkyne via hyperconjugative (direct) and conjugative (remote) effects, these effects can be weakened by the geometric constraints imposed by the twisted backbone of certain embodiments. Structural reorganization in the transition state (TS) may remove these constraints and unlock the power of remote electronic effects for selective TS stabilization.

Not wishing to be bound by any particular theory, it is believed that the introduction of a twisted chiral backbone into a cycloalkyne typically requires larger cycles (i.e., cyclodecynes), which may be intrinsically less strained than smaller cycloalkynes. The loss of strain associated with the larger cycles may increase the importance of using stereoelectronic effects for the activation of cyclodecynes towards click cycloadditions.

For the compounds and methods disclosed herein, more than one reaction scheme may be provided for preparing a compound. The reaction schemes that are not specifically provided for the preparation of a stated compound are applicable for its synthesis, if the appropriate substitutions can be provided for in the precursors, starting materials, or reagents employed in that scheme.

Although any methods, devices, and materials similar or equivalent to those described herein can be used in the practice or testing of the invention, the typical methods, devices and materials are herein described. All publications and patents mentioned in the disclosure of this invention are incorporated herein by reference, for the purpose of describing and disclosing, for example, the constructs and methodologies that are described in the publications, which might be used in connection with the presently described invention. The publications discussed above and throughout the text are provided solely for their disclosure prior to the filing date of the present application. Moreover, it is also to be understood that the terminology used herein is for the purpose of describing particular aspects or embodiments and is not intended to be limiting. Should the usage or terminology used in any reference that is incorporated by reference conflict with the usage or terminology used in this disclosure, the usage and terminology of this disclosure controls.

In one aspect, methods of making cyclodecynes are provided. In embodiments, the methods include [1] providing a 1,1'-biaryl compound substituted independently at the 2-position and the 2'-position with a hydroxyl or an amino group; and [2] contacting the 1,1'-biaryl compound with a protected but-2-yne-1,4-diol to form the cyclodecyne; wherein the amino group comprises a primary amine, a secondary amine, or a tertiary amine.

The protected but-2-yne-1,4-diol includes a protecting group that protects at least one of the hydroxyl functional groups. Both hydroxyl functional groups may be protected with the same type of protecting group, or each hydroxyl functional group may be protected with a different type of protecting group. Any protecting group known in the art that is compatible with the methods provided herein may be used. In some embodiments, the protecting groups include tosylate (Ts) protecting groups. In some embodiments, the protecting groups include nosylate (Ns) protecting groups.

Generally, the contacting of a 1,1'-biaryl compound with a protected but-2-yne-1,4-diol may occur at any temperature effective to form a product. In some embodiments, the contacting occurs at ambient (i.e., room) temperature. In some embodiments, the temperature at which the contacting occurs is about 0° C. to about 40°, about 10° C. to about 40° C., about 20° C. to about 40° C., or about 20° C. to about 30° C. In some embodiments, the contacting occurs at ambient pressure. In some embodiments, the contacting occurs at ambient temperature and at ambient pressure.

The contacting may occur in the presence of a base. Generally, any base that permits a reaction described herein to occur may be used. In some embodiments, the base includes $Cs_2CO_3$.

The contacting may occur in the presence of a liquid. Generally, any liquid that permits a reaction described herein to occur may be used. In some embodiments, the liquid includes dimethyl formamide (DMF), acetonitrile ($CH_3CN$), or a combination thereof.

In some embodiments, the contacting occurs in the presence of $Cs_2CO_3$, $CH_3CN$, dimethyl formamide (DMF), or a combination thereof. In some embodiments, the contacting occurs at ambient temperature, and in the presence of $Cs_2CO_3$, $CH_3CN$, dimethyl formamide (DMF), or a combination thereof. In some embodiments, the contacting occurs at ambient temperature and at ambient pressure, and in the presence of $Cs_2CO_3$, $CH_3CN$, dimethyl formamide (DMF), or a combination thereof.

The cyclodecynes produced by the methods provided herein may include an (R)-cyclodecyne, an (S)-cyclodecyne, or a combination thereof.

In some embodiments, a 1,1'-biaryl compound is substituted independently at the 2-position and the 2'-position with a hydroxyl or an amino group. The hydroxyl has the general structure "—OH", and the amino group may include a primary amine, a secondary amine, or a tertiary amine. The primary amine has the general structure "—$NH_2$". The secondary amine has the general structure "—$NHR^1$", wherein R' is a $C_1$-$C_{20}$ hydrocarbyl. In some embodiments, $R^1$ is a $C_1$-$C_{10}$ hydrocarbyl, a $C_1$-$C_5$ hydrocarbyl, or a $C_1$ hydrocarbyl. The tertiary amine has the general structure "—$NR'R^2$", wherein $R^1$ and $R^2$ are independently selected from a $C_1$-$C_{20}$ hydrocarbyl. In some embodiments, at least one of $R^1$ and $R^2$ is a $C_1$-$C_{10}$ hydrocarbyl, a $C_1$-$C_5$ hydrocarbyl, or a $C_1$ hydrocarbyl.

In embodiments, the 1,1'-biaryl compound has the following structure, which may be substituted or unsubstituted:

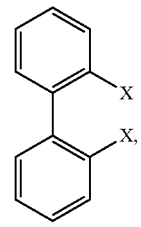

wherein X is selected independently from a hydroxyl or an amino group.

In some embodiments, the 1,1'-biaryl compound has the following structure, which may be substituted or unsubstituted:

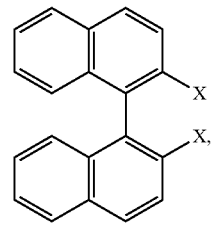

wherein X is selected independently from a hydroxyl or an amino group.

In some embodiments, the 1,1'-biaryl compound has the following structure, which is substituted at the 3-position, 6-position, 3'-position, and the 6'-position:

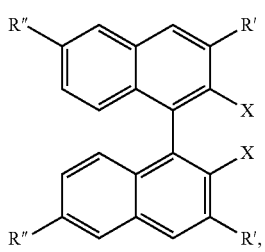

wherein X is selected independently from the hydroxyl or the amino group; and wherein R' and R" are independently selected from an alkoxy, an amino group, or an alkylsulfonate. In some embodiments, R' and R" are independently selected from an alkoxy, a tertiary amine, or an alkylsulfonate. The alkylsulfonate may have the following structure: —SO$_3$R''', wherein R''' is a $C_1$-$C_{20}$ hydrocarbyl. The alkoxy may have the following structure: —OR$^4$, wherein R$^4$ is a $C_1$-$C_{20}$ hydrocarbyl.

In some embodiments, the 1,1'-biaryl compound has the following structure, which may be substituted or unsubstituted:

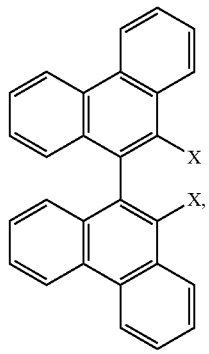

wherein X is selected independently from a hydroxyl or an amino group.

Although several of the foregoing 1,1'-biaryl structures are depicted in unsubstituted form, each 1,1'-biaryl may be substituted. A "substituted" 1,1'-biaryl is one in which one or more of the hydrogen atoms of the foregoing structures is replaced with a monovalent, substituted or unsubstituted, $C_1$-$C_{20}$ hydrocarbyl, any substituent described herein (such as those that may be present on a substituted $C_1$-$C_{20}$ hydrocarbyl), or a combination thereof.

The phrases "$C_1$-$C_{20}$ hydrocarbyl", "$C_1$-$C_5$ hydrocarbyl," "$C_1$ hydrocarbyl," and the like, as used herein, generally refer to aliphatic, aryl, or arylalkyl groups containing 1 to 20, 1 to 5, or 1 carbon atoms. Examples of aliphatic groups, in each instance, include, but are not limited to, an alkyl group, a cycloalkyl group, an alkenyl group, a cycloalkenyl group, an alkynyl group, an alkadienyl group, a cyclic group, and the like, and includes all substituted, unsubstituted, branched, and linear analogs or derivatives thereof, in each instance having 1 to about 20 carbon atoms, or 1 to about 5 carbon atoms, 1 carbon atom, etc. Examples of alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl.

Additional examples of alkyl moieties have linear, branched and/or cyclic portions (e.g., 1-ethyl-4-methyl-cyclohexyl). Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl. Examples of aryl or arylalkyl moieties include, but are not limited to, anthracenyl, azulenyl, biphenyl, fluorenyl, indan, indenyl, naphthyl, phenanthrenyl, phenyl, 1,2,3,4-tetrahydro-naphthalene, tolyl, xylyl, mesityl, benzyl, and the like, including any heteroatom substituted derivative thereof.

Unless otherwise indicated, the term "substituted," when used to describe a chemical structure or moiety, refers to a derivative of that structure or moiety wherein one or more of its hydrogen atoms is substituted with a chemical moiety or functional group such as alcohol, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), tertiary amine (such as alkylamino, arylamino, arylalkylamino), aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carboxyl, carboxylic acid, cyano, ester, ether (e.g., methoxy, ethoxy), halo, haloalkyl (e.g., —CCl$_3$, —CF$_3$, —C(CF$_3$)$_3$), heteroalkyl, isocyanate, isothiocyanate, nitrile, nitro, phosphodiester, sulfide, sulfonamido (e.g., SO$_2$NH$_2$, SO$_2$NR'R''), sulfone, sulfonyl (including alkylsulfonyl, arylsulfonyl and arylalkylsulfonyl), sulfoxide, thiol (e.g., sulfhydryl, thioether) or urea (—NHCONH-alkyl-).

In another aspect, cyclodecynes are provided herein. The cyclodecynes include those that may be made according to embodiments of the methods described herein. In some embodiments, the compounds have a structure according to one of the following formulas:

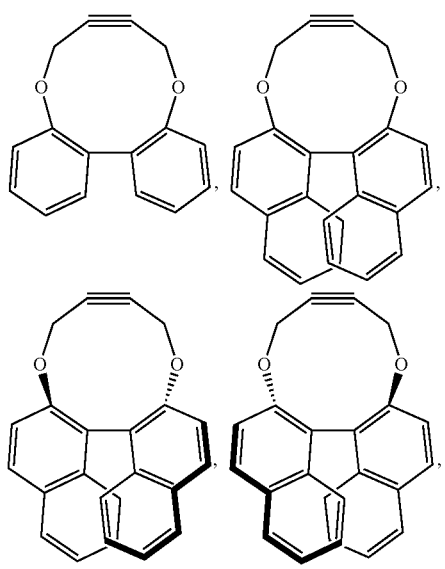

-continued

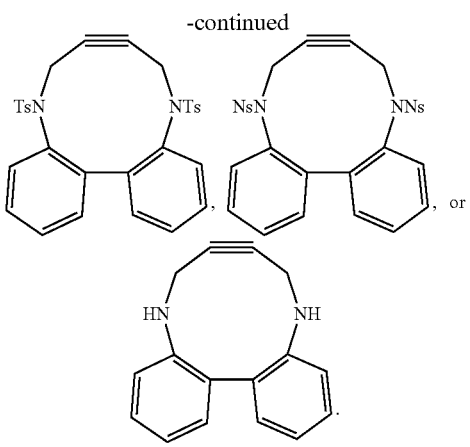

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

In the descriptions provided herein, the terms "includes," "is," "containing," "having," and "comprises" are used in an open-ended fashion, and thus should be interpreted to mean "including, but not limited to." When methods and composite materials are claimed or described in terms of "comprising" various components or steps, the composite materials and methods can also "consist essentially of" or "consist of" the various components or steps, unless stated otherwise.

The terms "a," "an," and "the" are intended to include plural alternatives, e.g., at least one. For instance, the disclosure of "a 1,1'-biaryl," "a protecting group," "a substituent", and the like, is meant to encompass one, or mixtures or combinations of more than one 1,1'-biaryl, protecting group, substituent, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in one embodiment, that the temperature at which the contacting occurs is about 20° C. to about 30° C. This range should be interpreted as encompassing temperatures of about 20° C. and 30° C., and further encompasses "about" each of 21° C., 22° C., 23° C., 24° C., 25° C., 26° C., 27° C., 28° C., and 29° C., including any ranges and sub-ranges between any of these values.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Characterization and Instrumentation:

Circular Dichroism spectra were obtained using an AVIV 410 CD spectrometer with a 2 mm×4 cm quartz cuvette in methylene chloride. The UV-visible spectra were recorded at room temperature using an Agilent Cary 60 UV-Visible spectrophotometer with a 1 cm×4 cm quartz cuvette in methylene chloride.

All measurements were performed with neat solvent as the blank. All calculations were performed with Gaussian '09 D.01. The (SMD=solvent)/M06-2X(D3)/6-311++G(d,p) level of theory was used; SMD=$H_2O$ was used for the preliminary calculations and ring strain evaluations, whereas SMD=$CHCl_3$ was used for all remaining calculations.

NBO6 was used to evaluate $2^{nd}$ order perturbation interactions at the (SMD=$CHCl_3$)/M06-2X(D3)/6-311++G(d,p) level of theory. Due to basis set size restrictions, deletions were performed at the (SMD=$CHCl_3$)/HF/6-311G(d,p) level of theory with NBO6 interfaced with Gaussian '09.

Example 1—Synthesis of Cyclodecynes

A series of compounds were made in which the chiral architecture and the endocyclic heteroatoms were incorporated into the cycle from commercially available 2,2'-biaryl nucleophiles.

The compounds of this example were made according to the following scheme:

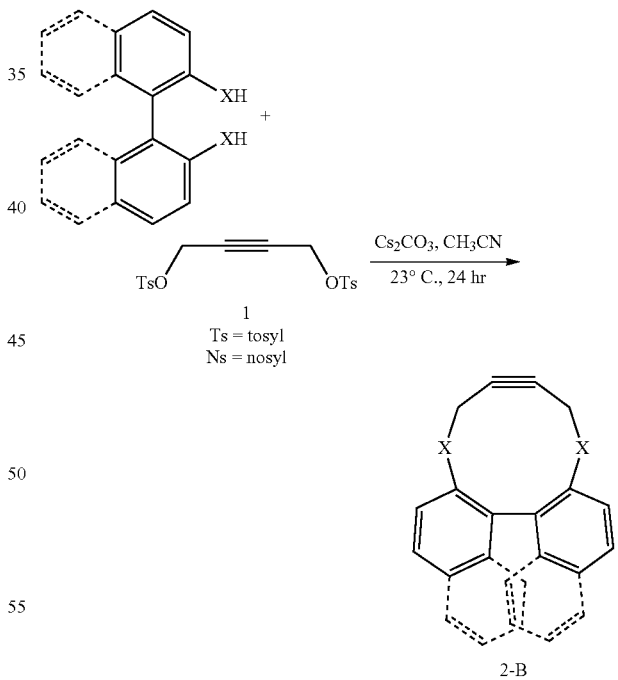

In this example, direct access to the cycloalkyne was feasible through the favorable combination of the mild base and low ring strain of cyclodecyne products. Furthermore, the use of mild base prevented the undesired alkyne-allene isomerization. Cesium carbonate was found to be a suitable base for the cyclization.

The products produced in this example are depicted at the following table, along with their respective yields.

| Product Name, Ref. No. | Product Structure/Yield |
|---|---|
| BIPOC, 2 | 68%[1] |
| rac-BINOC, 3 | 79%[1]<br>68%, ~1.6 g recrystallized<br>2 g scale |
| 99%-(R)-BINOC, 4 | 80%[1]<br>63%, ~1.5 g recrystallized<br>2 g scales |
| 99%-(S)-BINOC, 5 | 79%[1] |
| BIPAC-Ts, 6 | 73%[1,2] |
| BIPAC-Ns, 7 | 44%[1,2] |
| BIPAC, 8 | 32%[2,3,4] |

[1] NMR yield determined using an internal standard.
[2] DMF, 35° C., 72 hr.
[3] Isolated yield
[4] One-pot cyclization deprotection.

Bis-tosylate of but-2-yne-1,4-diol 1 was a readily available electrophile (22 grams of 1 were prepared in a one-step, 98% yield operation) with good reactivity towards heteroatomic nucleophiles.

Its reaction with 2,2'-biphenol gave the target 2,2'-biphenyldioxacyclodecyne (BIPOC) 2 in a 68% isolated yield. The optimized cyclization conditions were extended to the more sterically demanding racemic 2,2'-binaphthol (BINOL) to obtain rac-2,2'-binaphthyldioxacyclodecyne (rac-BINOC) 3 in 79% yield.

The individual (R)- and (S)-enantiomers of BINOL (~99% purity) gave enantiopure (R)-BINOC 4 and (S)-BINOC 5 in 80% and 79% yields, respectively, without loss of chiral integrity as indicated by circular dichroism (CD) spectroscopy (FIG. 1). FIG. 1 depicts the overlap of CD spectra for (R)-BINOC and (S)-BINOC.

To compare the effect of endocyclic heteroatoms on reactivity, also prepared were the nitrogen analogues BIPAC-Ts 6 and BIPAC-Ns 7, from the corresponding bis-tosylate and bis-nosylate of 2,2'-biphenyldiamine. Under these conditions, the direct use of 2,2'-biphenyldiamine gave recovered starting diamine and tosylate, presumably due to lower nucleophilicity of unsubstituted anilines. However, a one-pot cyclization-deprotection sequence with the more reactive nosylate produced the free bis-amine 8 (2,2'-biphenyldiaminocyclodecyne, BIPAC) in 32% yield.

Twisting and bending of the cyclodecynes were elucidated with X-ray analysis and computations. The following depicts a summary of X-ray and solvent-corrected DFT geometries. DFT values ((SMD=CHCl$_3$)/M06-2X(D3)/6-311++G(d,p) level of theory) are in parenthesis.

| Cyclodecynes (2, 3, 4, 6, 8) | Alkyne torsion (CCCC) Φ2 | Chameleonic torsion (CXCC) Φ2 | Biaryl torsion (CCCC) Φ3 | Alkyne bending (CCC) |
|---|---|---|---|---|
| BIPOC | 14.6 (19.9) | 105[1] (101) | 114 (116) | 166 (166) |
| rac-BINOC | 18.9 (14.3) | 107 (108) | 110 (108) | 165 (165) |
| (R)-BINOC, mol1 | 9.3 | 109 | 109 | 164 |
| (R)-BINOC, mol2 | 25.1 | 105 | 109 | 166 |
| (R)-BINOC, mol3 | 20.9 | 111 | 107 | 163 |
| BIPAC-Ts[2] | 25.6 (8.5) | 99 (105) | 115 (108) | 169 (169) |
| BIPAC | 4.4 (5.2) | 106 (106) | 107 (107) | 166 (165) |

[1]Angles are in degrees and shown as the absolute values.
[2](SMD = CHCl3)/M06 − 2X(D3)/6-31 + G(d, p) level for BIPAC-Ts.

Figure 2:
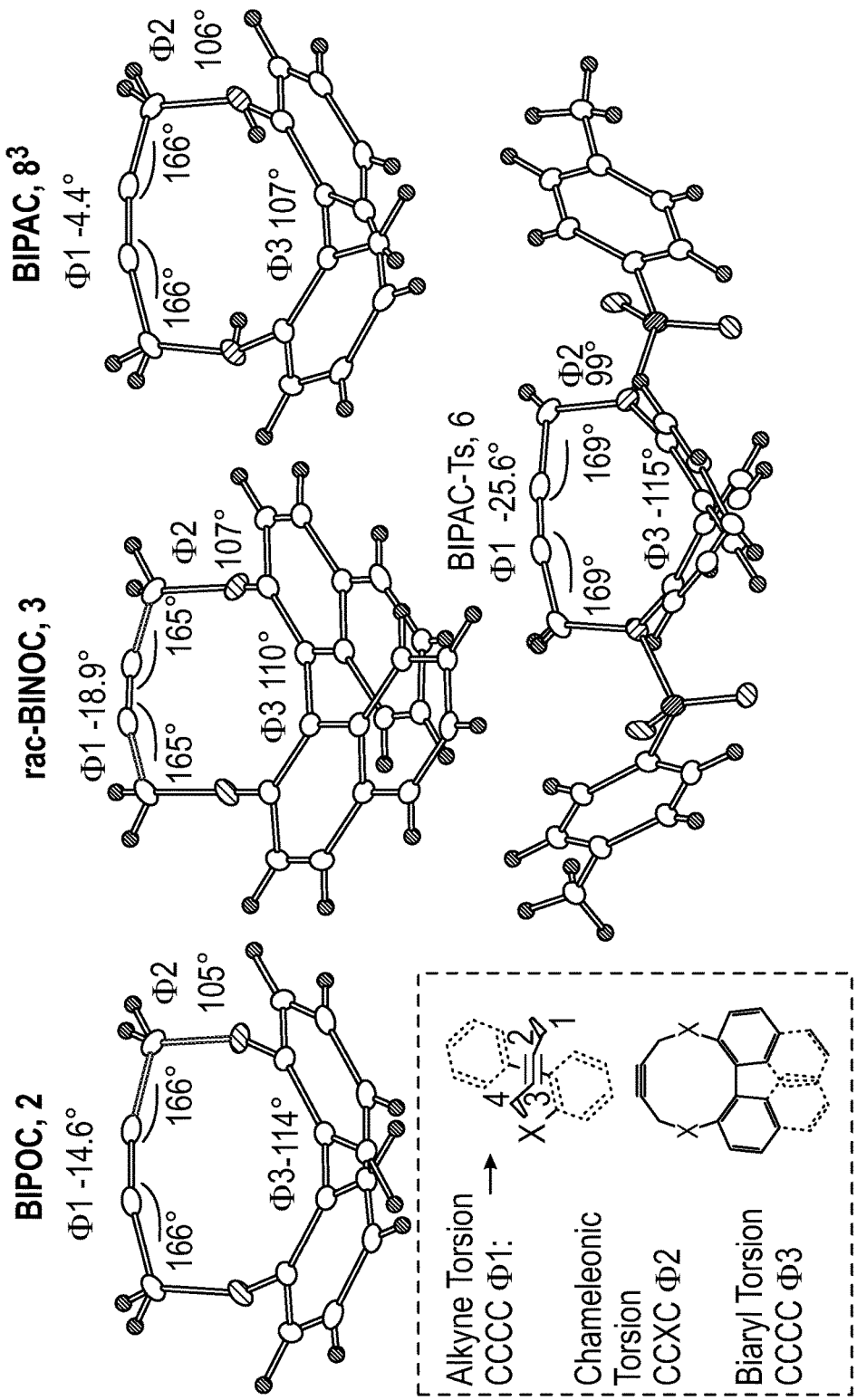
FIG. 2 depicts Oak Ridge Thermal-Ellipsoid Plot Program (ORTEP) results for embodiments of several compounds, and various twisting modes in embodiments of chiral cyclodecynes (inset).

FIG. 2 depicts Oak Ridge Thermal-Ellipsoid Plot Program (ORTEP) results of BIPOC, rac-BINOC, BIPAC, and BIPAC-Ts. Ellipsoids are at the 50% probability level. All non-hydrogen atoms were refined anisotropically, while all hydrogen atoms were placed in their geometrically calculated positions and fixed. Various twisting modes in chiral cyclodecynes are depicted in the inset of FIG. 2: alkyne torsion, chameleonic torsion and biaryl torsion. BIPAC has a similar framework ($C_{(sp2)}$—NH—CH$_2$-$C_{(sp)}$) to cyclononyne ABSACN (Hagendorn, T. et al., *RSC Adv.* 4, 15493 (2014)), however, the cyclononyne is more bent (159°).

The magnitude of alkyne bending(163-169°) was comparable to that in known cyclononynes (see, e.g., Ni, R. et al., *Angew. Chem. Int. Ed.* 54, 1190 (2015)). The alkyne torsions Φ$_1$ ranged from 4° to 25°, which indicated trans-bent geometry, an apparently new structural distortion in cycloalkynes. The "chameleonic" torsion Φ2 showed the alignment of the $C_{(sp3)}$—X bonds with the aryl ring and appeared to reflect delocalization (or lack thereof) of heteroatom lone pairs into the aryl ring. In the near-perpendicular observed geometries (99° to) 111° the heteroatoms p-type lone pair was misaligned with the aromatic π-system. The biaryl torsions Φ3 ranged from 107° to 115°, which was much closer to the perpendicular geometry than 2,2'-biphenol (torsion angle of 48°).

Figure 3:
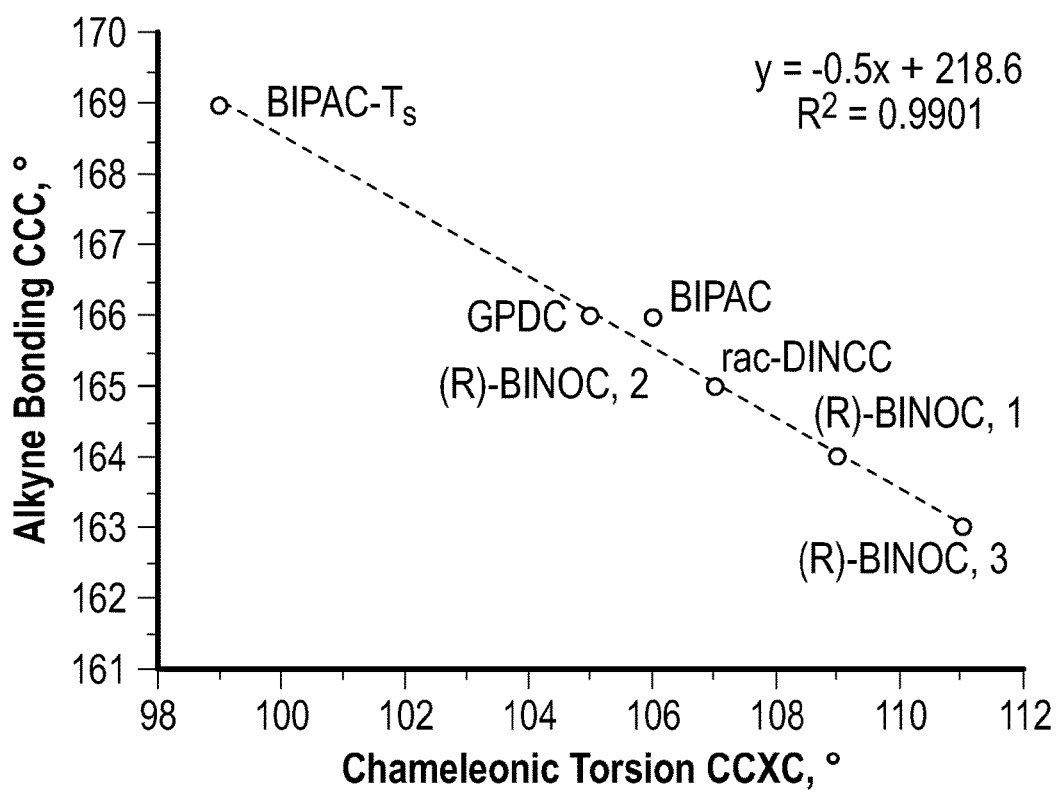
FIG. 3 depicts a correlation of chameleonic torsion and alkyne bending using X-ray data.

Remarkably, crystal data of (R)-BINOC revealed three distinct molecules (mol1, mol2, mol3) in the asymmetric unit cell. The variable geometries observed for the three molecules of (R)-BINOC indicated the backbone cyclodecynes were, in this example, sufficiently flexible to respond to changes in chemical environment. Analysis of the structural parameters for the cyclodecynes revealed a strong correlation between "chameleonic" torsion Φ2 and alkyne bending, as depicted at FIG. 3: forcing the $C_{(sp3)}$—X bonds to be orthogonal to the aryl ring partially alleviated alkyne bending. FIG. 3 depicts a correlation of chameleonic torsion and alkyne bending using X-ray data.

Figure 4:
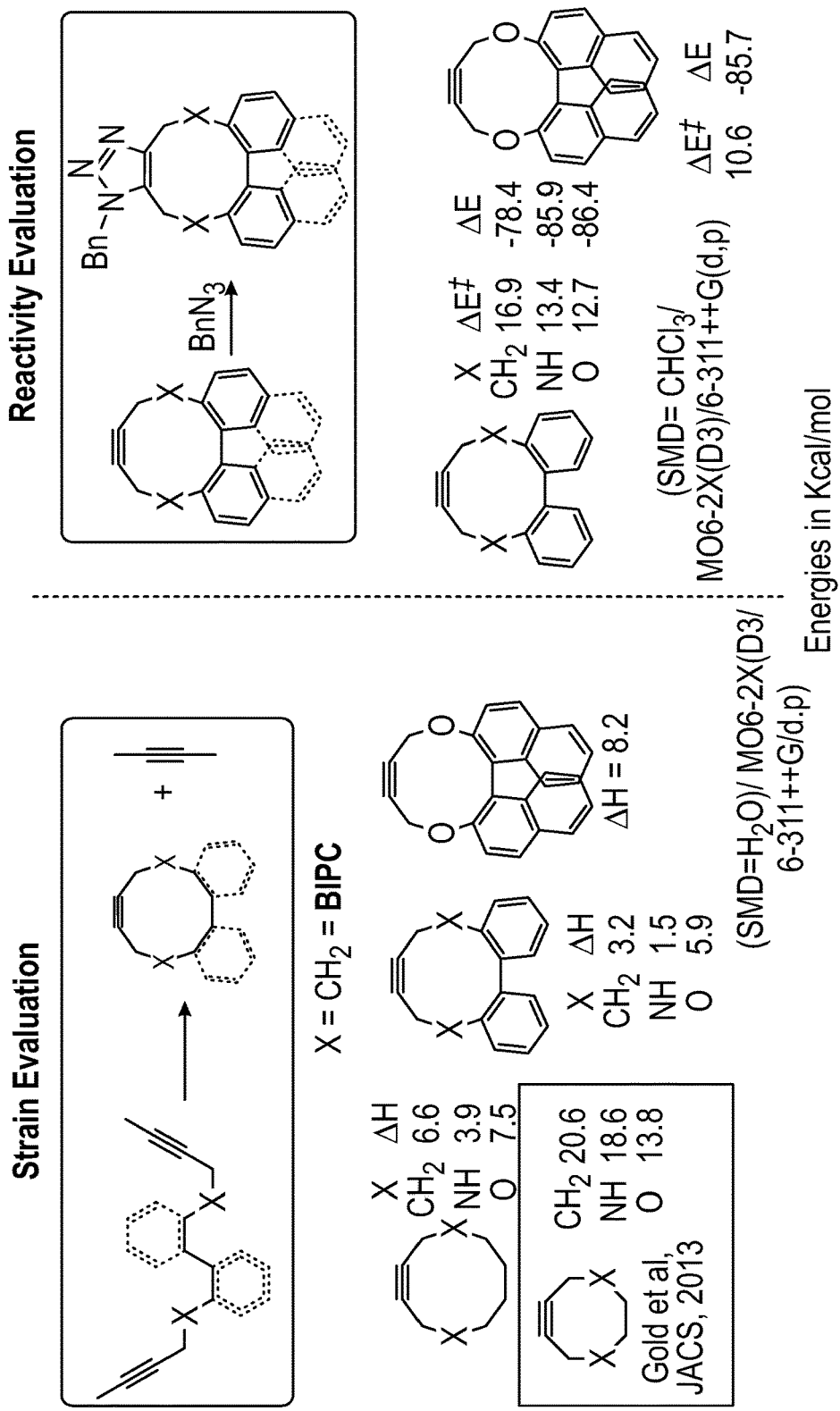
FIG. 4 depicts the results of a computational evaluation of strain and reactivity using isodesmic equations and activation energies, respectively.

Computations were used to quantify the effect of strain on reactivity of four twisted cyclodecynes including the carbocyclic analogue biphenylcyclodecyne (BIPC). In sharp contrast to the analogous endo-substituted cyclooctynes, the presence of endocyclic oxygen atoms did not alleviate strain relative to BIPC (FIG. 4, left).

This finding was attributed to the twisted geometry adopted by the starting materials where the C—X bond must make a choice whether to align with the aryl group or with the alkyne. Another stark difference to cyclooctynes was that ring fusion decreased the cyclodecyne strain energy (by ~2-3 kcal/mol). This behavior was attributed to the removal of torsion strain and transannular interactions.

Initially, the reactivity of cyclodecynes was evaluated from competition between BIPOC and an analogous electronically activated acyclic alkyne towards benzyl azide. In agreement with the superior reactivity of BIPOC, less than 1% of the product was derived from the linear alkyne as per $^1$H-NMR analysis of the reaction mixture. Furthermore, cycloaddition with the azide in the presence of an equimolar amount of thiol, a common competing trap for cyclooctynes under biological conditions, gave 92% of the triazole product.

Experimental 2$^{nd}$ order rate constants and activation parameters provided quantitative evaluation of the click reactivity of twisted cyclodecynes BIPOC, BINOC, BIPAC-Ts, and BIPAC in reaction with benzyl azide, as depicted at the following table.

| Alkyne | k (M$^{-1}$ s$^{-1}$) | Δ E$^{\neq}_{exp}$ | Δ H$^{\neq}_{exp}$ | Δ G$^{\neq}_{exp, 37 °C}$ |
|---|---|---|---|---|
| BIPOC, 2[1] | 0.159 × 10$^{-3}$ (±2.51E−06) | 12.1 | 11.4 | 23.0 |
| rac-BINOC, 3 | 0.621 × 10$^{-3}$ (±1.07E−05) | 10.7 | 10.1 | 22.2 |
| BIPAC, 8 | 0.176 × 10$^{-3}$ (±3.46E−07) | 13.7 | 13.1 | 22.9 |
| BIPAC-Ts, 6 | 0.007733 × 10$^{-3}$ (±1.75E−07) | 16.4 | 15.8 | 24.7 |

[1]The 2$^{nd}$ order rate constant with benzyl azide at 25° C. in CD$_3$CN is 0.18 × 10$^{-3}$ M$^{-1}$ s$^{-1}$.

Experimental 2$^{nd}$ order rate constants were determined through $^1$H-NMR kinetics with benzyl azide at 25° C. in CDCl$_3$ and activation parameters (in kcal/mol). Kinetic experiments were performed in triplicate and the average rate is reported.

These experimental trends were corroborated with computational analysis. FIG. 4 depicts the results of a computational evaluation of strain and reactivity using isodesmic equations and activation energies, respectively.

Figure 5:
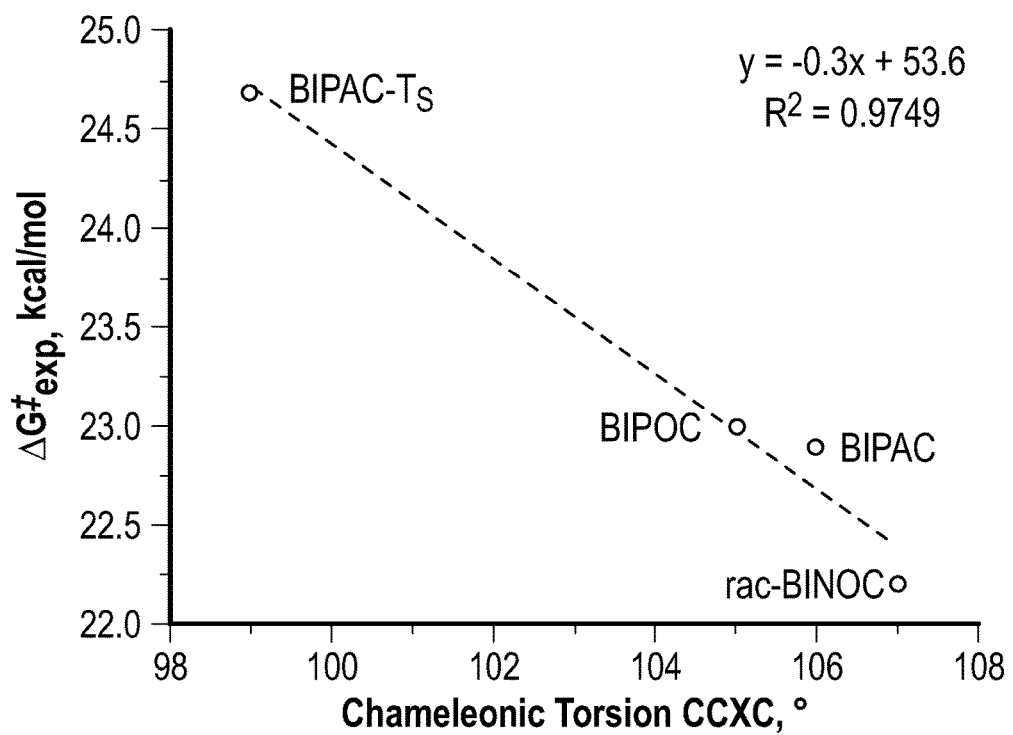
FIG. 5 depicts a correlation between X-ray chameleonic torsion and experimental $\Delta G^{\ddagger}$ for embodiments of compounds described herein.

Although endocyclic acceptors have a different effect on ring strain, they increased reactivity similar to the way they activate cyclooctynes (Gold, B. et al., *J. Am. Chem. Soc.* 135, 1558 (2013)) and cyclononynes (Ni, R. et al., *Angew. Chem. Int. Ed.* 54, 1190 (2015)) suggesting a common TS stabilizing effect, i.e., hyperconjugation. The enthalpy of activation for BIPOC was low (11.4 kcal/mol) but, as expected for a bimolecular process, the unfavorable entropic contribution raised the free energy of activation (23.0 kcal/mol at 37° C.). BINOC with an enthalpy of activation of 10.7 kcal/mol was about 10-fold more reactive than BIPOC. The experimental kinetics suggested strong correlation between free energy of activation and "chameleonic" torsion Φ2, as depicted at FIG. 5. FIG. 5 depicts a correlation between X-ray chameleonic torsion and experimental ΔG$^{\ddagger}$ for BIPOC, BINOC, BIPAC-Ts, and BIPAC.

It appears that the more the molecules were twisted from the perpendicular geometry, the lower was the activation barrier.

Figure 6:
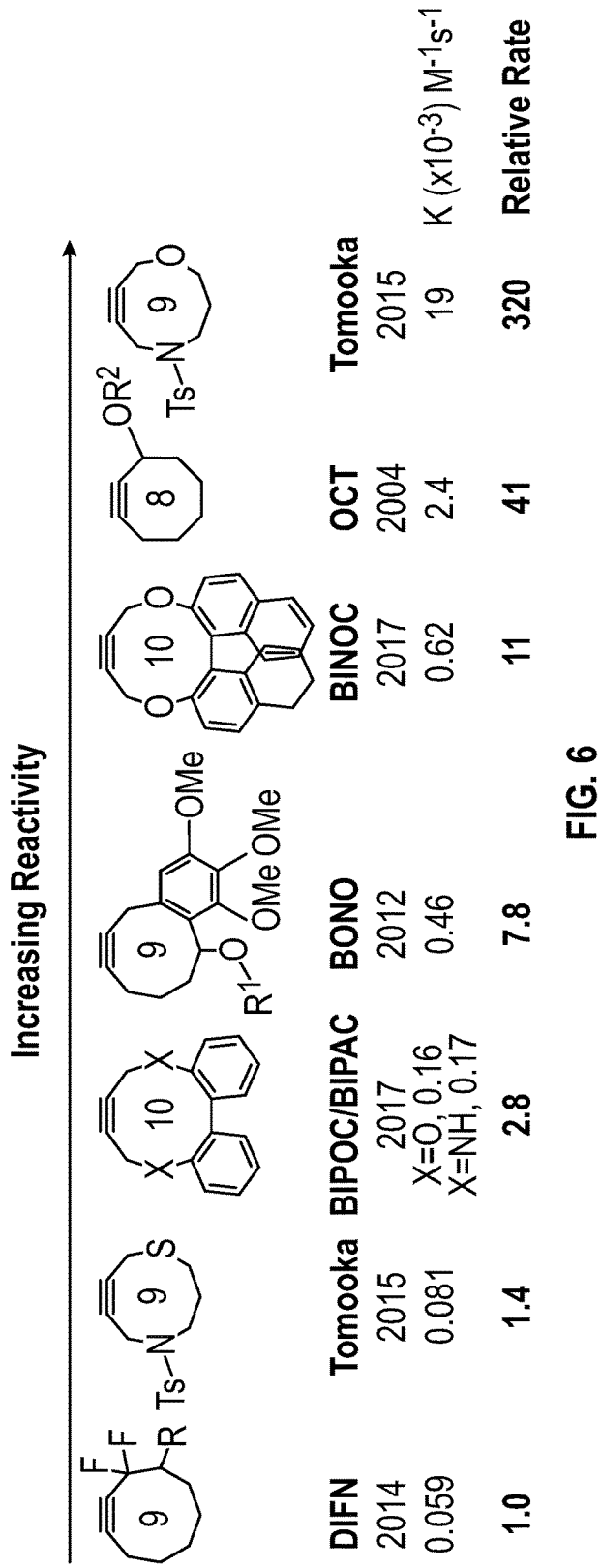
FIG. 6 depicts literature precedents of non-catalyzed cycloadditions of alkynes with benzyl azide.

It was instructive to compare the reactivity of BIPOC and BINOC with known cycloalkynes, as depicted at FIG. 6. FIG. 6 depicts literature precedents of non-catalyzed cycloadditions of alkynes with benzyl azide (Agard, N. J. et al., *J. Am. Chem. Soc.* 126, 15046 (2004); Ni, R. et al., *Angew. Chem. Int. Ed.* 54, 1190 (2015); Kolb, H. C. et al., *Angew. Chem. Int. Ed.* 40, 2004 (2001); and Thirumurugan, P. et al., *Chem Rev.* 113, 4905 (2013)). All kinetics displayed second-order rate constants $M^{-1}s^{-1}$ at 25° C. in $CD_3CN$. BIPOC and BINOC rate constants reported are in $CDCl_3$. The changes in reactivity for BIPOC in different solvents were small.

Twisted cyclodecynes outcompeted many of their smaller rivals, such as cyclononynes. For example, BINOC was ~11-fold more reactive than difluorinated cyclononyne (DIFN) and ~7-fold more reactive than an activated cyclononyne with endocyclic nitrogen and sulfur atoms. Furthermore, BINOC reacted only four times slower than OCT, a monosubstituted cyclooctyne. Surprisingly, when a strong acceptor $C_{(sp3)}$—O was exchanged for a weaker $C_{(sp3)}$—N acceptor (BIPOC→BIPAC), neither the experimental rate nor the free energy of activation changed. A small increase in the activation enthalpy was completely offset by the more favorable activation entropy in BIPAC.

Furthermore, BIPAC-Ts reacted with benzyl azide ~100-fold slower than BIPAC. This observation further contradicted the expectation that a stronger acceptor should increase reactivity. The lower reactivity of BIPAC-Ts agreed well with an activation enthalpy of 15.8 kcal/mol and the decreased alkyne angle strain(169°) in the X-ray geometry.

Figure 7:
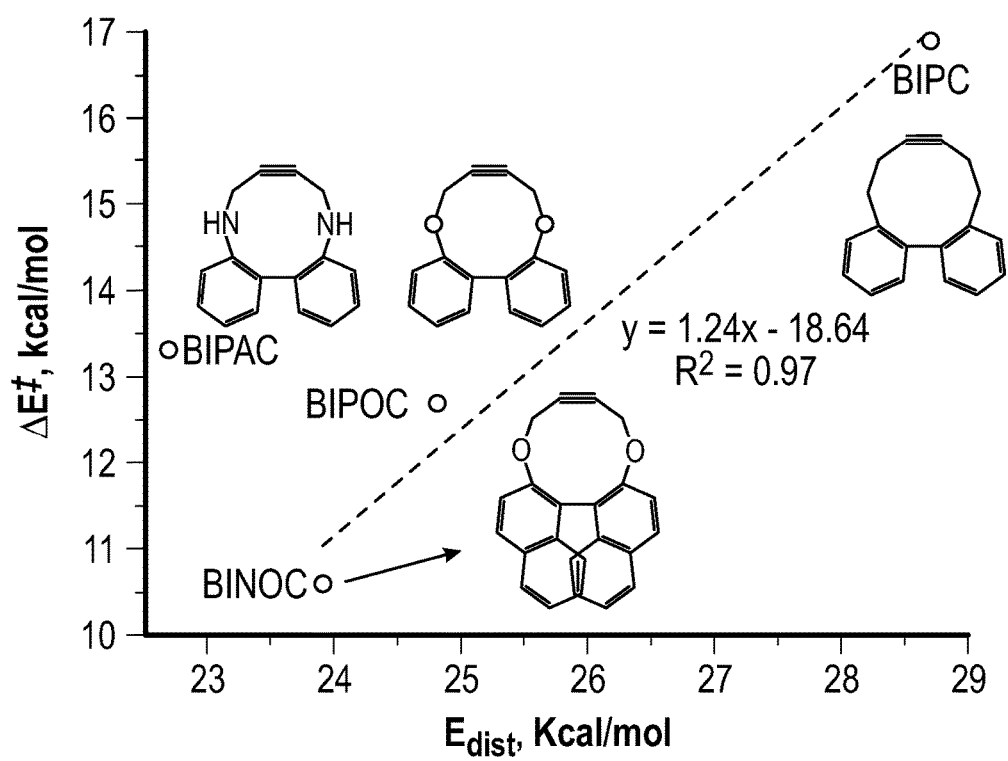
FIG. 7 depicts a correlation of total distortion energy and activation energy for an embodiment of a compound described herein.

Distortion-interaction energy analysis (FIG. 7) revealed that, relative to the all-carbon analogue BIPC, the endocyclic acceptors lowered total distortion energies. FIG. 7 depicts a correlation of total distortion energy and activation energy.

This trend appeared to be consistent with hyperconjugative assistance of propargylic C—X acceptors to alkyne bending and alkyne-azide bond formation (Gold, B. et al., J. Am. Chem. Soc. 135, 1558 (2013)). However, BIPAC did not follow the usually observed correlation between the activation barrier and the total distortion penalty. Although BIPAC's alkyne geometry distorted the most from the ground state geometry in the TS (166° to 159°), paradoxically this TS also had the lowest total distortion energy among the four entries depicted at the following table, which depicts activation, interaction, and distortion energies.

| Alkyne | $\Delta E^\neq_{calc}$ | $\Delta E_{rxn}$ | $E_{int}$ | $E_{azide\ dist}$ | $E_{alkyne\ dist}$ | $E_{total\ dist}$ |
|---|---|---|---|---|---|---|
| BIPC | 16.9 | −78.4 | −11.8 | 22.5 | 6.2 | 28.7 |
| BIPAC | 13.4 | −85.9 | −9.3 | 18.7 | 4.0 | 22.7 |
| BIPOC | 12.7 | −86.4 | −12.1 | 20.8 | 4.0 | 24.8 |
| BINOC | 10.6 | −85.7 | −13.3 | 20.4 | 3.5 | 23.9 |

The paradoxical features of BIPAC likely stemmed from unique constraints that twisted cyclodecynes imposed on the propargylic heteroatoms connected to the biaryl core. Each C—X moiety was sandwiched between the triple bond and the aryl group.

Figure 8:
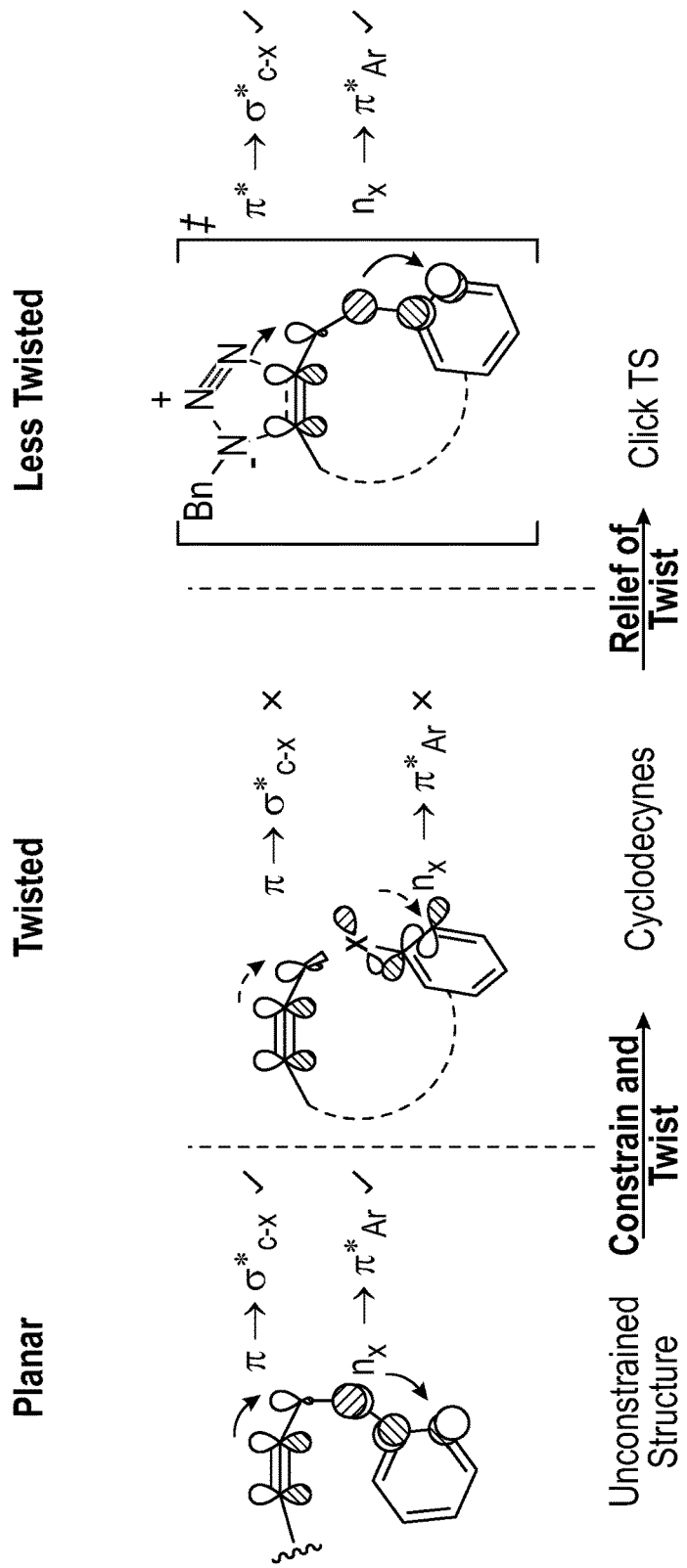
FIG. 8 is a depiction of how structural changes of embodiments of cyclodecynes may affect hyperconjugation and conjugation.

In the absence of structural constraints, the C—X bridge was expected to play contrary electronic roles towards functionalities at its opposing ends: serve as a $\sigma^*_{C-X}$ acceptor (hyperconjugation) relative to the alkyne but act as the $n_X$ donor relative to the aryl group (conjugation). Due to the geometric constraint in the twisted cycloalkyne framework, both interactions were believed to be weakened. As the cyclodecynes structurally reorganized in the TS, these conjugative interactions were strengthened (FIG. 8). FIG. 8 is a depiction of how structural changes of cyclodecynes may affect hyperconjugation and conjugation.

The conjugative $n_X \to \pi_{CCaryl}^*$ interactions were quantified with NBO analysis by deleting the orbital specific interactions and recalculating the wavefunction energy. Although the usual conjugation ($n_X \to \pi_{CCaryl}^*$) was weakened in the cycloalkynes by geometric constraints, this interaction increased in the TS.

For oxygen, which has two lone pairs, conjugation could not be completely switched off in the cycloalkyne, and the change from GS to TS was moderate as reflected in a 4 kcal/mol increase in the NBO energies of the respective interactions ($\Delta E_{del}$).

Figure 9:
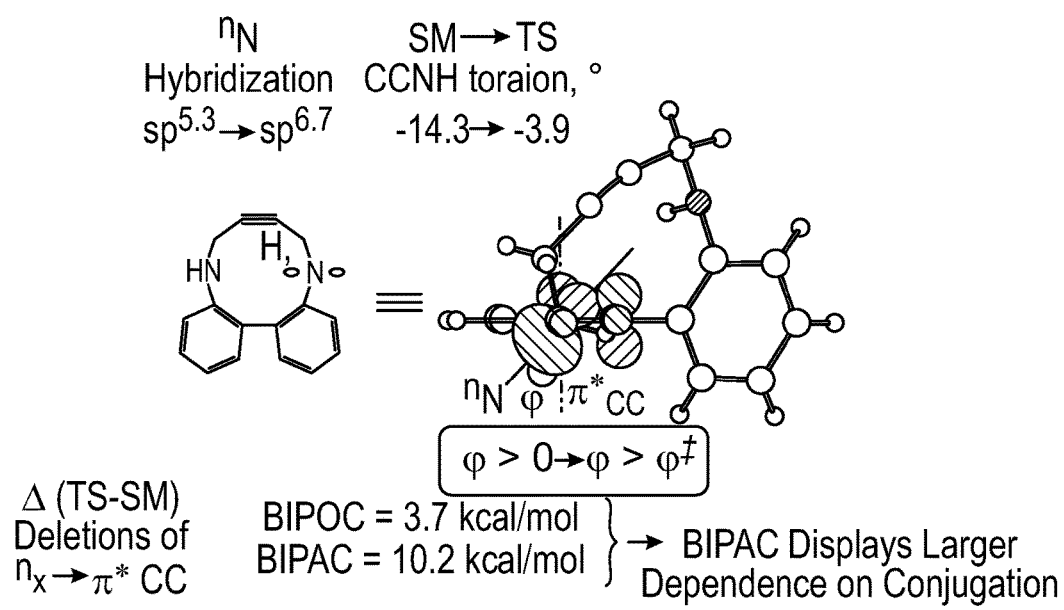
FIG. 9 depicts an evaluation of one embodiment of a compound described herein.

However, unlike oxygen, nitrogen has only one lone pair and the change in NBO ($n_N \to \pi_{CCaryl}^*$) conjugation energy was much larger ($\Delta E_{del}$~10 kcal/mol) (FIG. 9). FIG. 9 depicts an evaluation of conjugation via NBO deletions of $n_N \to \eta_{CCaryl}^*$ interactions for BIPOC and BIPAC, and geometric changes account for BIPAC's reactivity.

The geometric assistance to resonance was further facilitated by rehybridization[i] of the nitrogen lone pair (sp⁵ to sp⁷). This increase in conjugative stabilization through the activation of remote stereoelectronic interactions likely explained the low total distortion energy in the TS for BIPAC.

Figure 10:
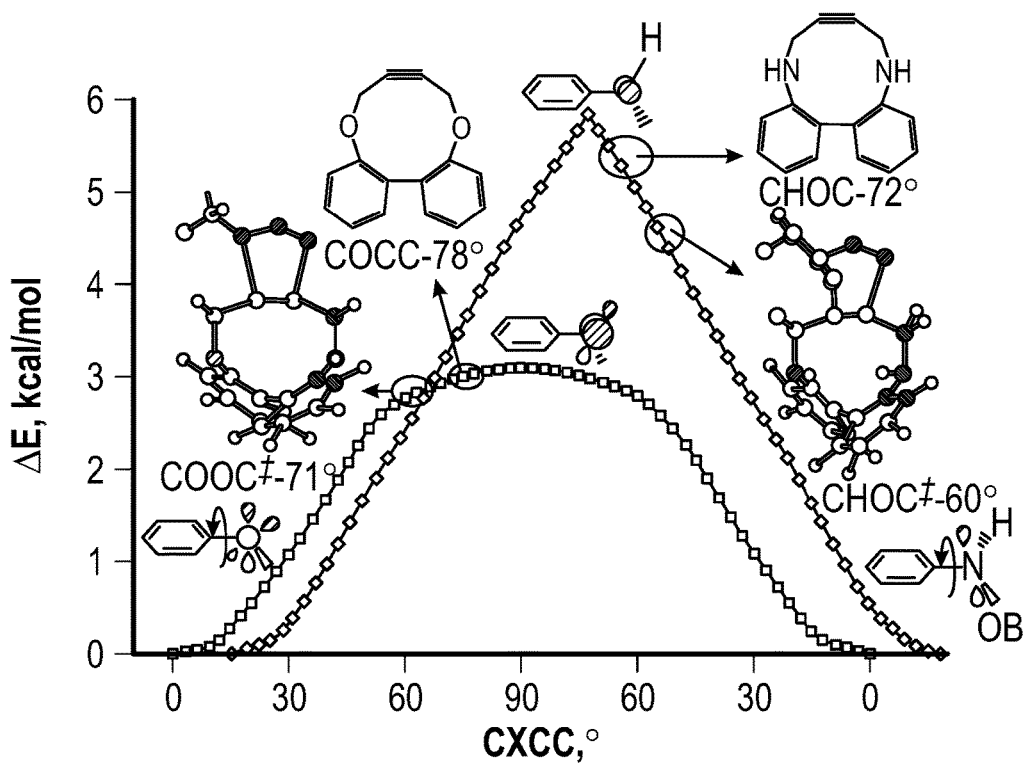
FIG. 10 depicts CXCC dihedral scans for anisole and N-methylaniline.

Because NBO interaction energy quantified only a single component from the complex combination of electronic, electrostatic and structural effects the total energy cost of distortions discussed above was evaluated using dihedral scans shown at FIG. 10. FIG. 10 depicts CXCC dihedral scans for anisole (X=O, squares) and N-methylaniline (X=N, diamonds). The CXCC dihedrals for BIPOC and BIPAC are shown in their respective parent systems' PES in order to illustrate their "stored" energy. CXCC[‡] indicates dihedrals for their respective click reactions transition states.

The chameleonic torsions for BIPOC and BIPAC (78° and 72°, respectively) indicated the presence of stored energy facilitated by the geometric constraint of a strained cycle. Computational analysis confirmed that the out-of-plane C—X bonds rotated in the TS to become less twisted and increased conjugation with the aryl rings. Such change brought only 0.2 kcal/mol (~0.1×2) for BIPOC where, due to the presence of two lone pairs at the oxygen atoms, the resonance could not be completely switched off by rotation. However, stabilization was much larger (~2 kcal/mol) for BIPAC, a better "chameleon". Increased reactivity of BIPAC revealed that the modulation of aniline resonance by structural constraints found a new role in alkyne cycloadditions.

Figure 11:
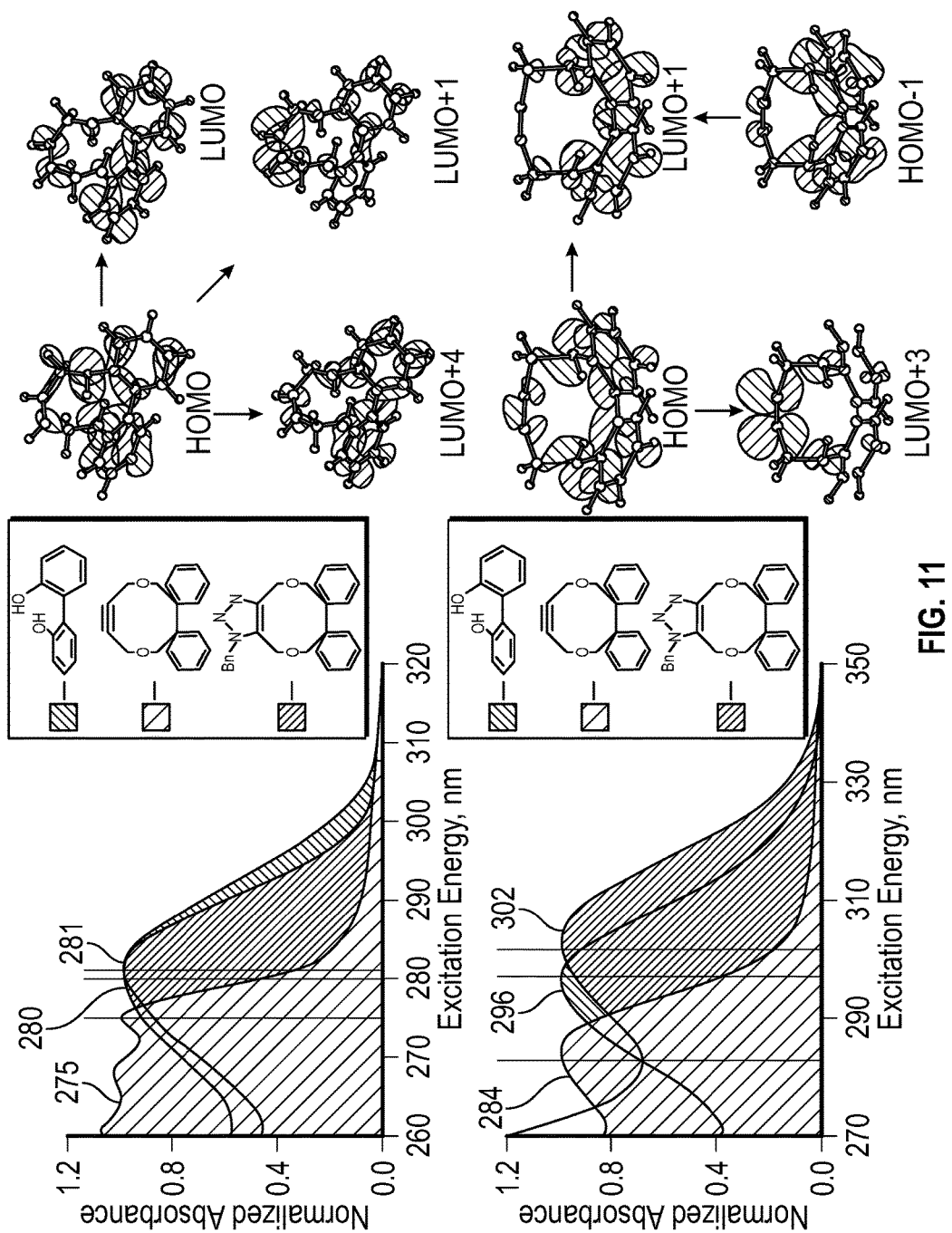
FIG. 11 depicts (at left) experimental UV-VIS spectra of embodiments of compounds described herein, corresponding triazole products (normalized absorptions), and (at right) selected molecular orbitals involved in certain transitions of an embodiment of a compound described herein and a less twisted alkene analog.

An independent experimental confirmation for the suggested changes in conjugation between the starting 2,2' biaryl nucleophiles, cyclodecynes and the triazole products was provided by UV-VIS spectroscopy, as depicted at FIG. 11. FIG. 11 depicts (at left) experimental UV-VIS spectra of 2,2'-biaryl nucleophiles, BIPOC, BIPAC, and corresponding triazole products (normalized absorptions). For the calculated TD-DFT UV-VIS spectra of 2,2'-biaryl nucleophiles, BIPOC, BIPAC, and corresponding products that show the identical trend. At right, FIG. 11 depicts selected MOs involved in the TD-DFT transitions of BIPAC and its less twisted alkene analog.

In the cyclodecynes, where the lone pairs were misaligned due to geometric restraint, a hypsochromic shift was observed relative to the acyclic structures where the lone pairs could have unobstructed communication with the aryl rings. The azide/alkyne click reaction partially relieved the twisting of the backbone and restored the lone pair/biphenyl communication, which was believed to cause a bathochromic shift in the triazole product relative to the alkyne. These findings were fully supported by the trends in the computed spectra that reproduced the magnitude of the spectral shifts and illustrated that the heteroatom lone pairs were involved in the multiconfigurational excitations.

In this example, twisted cyclodecynes were stable crystalline compounds available via a mild and scalable one-step synthetic procedure. They were isolated by filtration and purified by recrystallization.

In the present examples, the embedded heteroatoms provided transition state stabilization during the click reaction with azides via a combination of hyperconjugative acceptor and conjugative donor effects. In particular, the aza-cyclodecyne BIPAC drew increased reactivity from a remote stereoelectronic effect based on modulation of aniline resonance. Until now, such remote activation was believed to be unrecognized in chemistry.

The invention claimed is:

1. A method of making a cyclodecyne, the method comprising:
   providing a 1,1'-biaryl compound substituted independently at the 2-position and the 2'-position with a hydroxyl or an amino group; and
   contacting the 1,1'-biaryl compound with a protected but-2-yne-1,4-diol to form the cyclodecyne;
   wherein the amino group comprises a primary amine, a secondary amine, or a tertiary amine;
   wherein the 1,1'-biaryl compound has a structure according to one of the following formulas, which may be substituted or unsubstituted—

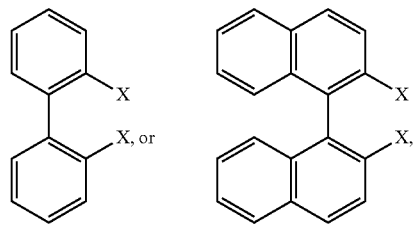

wherein X is selected independently from the hydroxyl or the amino group; and
wherein the cyclodecyne has a structure according to one of the following formulas—

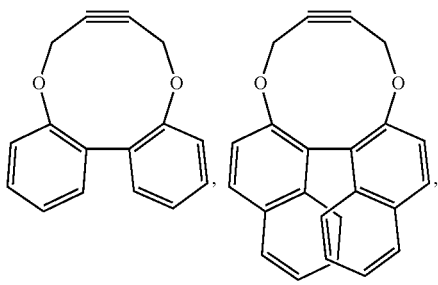

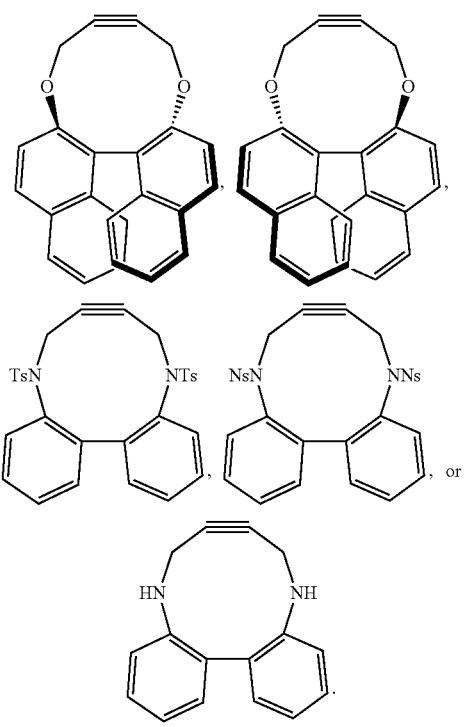

2. The method of claim 1, wherein the protected but-2-yne-1,4-diol comprises tosylate protecting groups.

3. The method of claim 1, wherein the protected but-2-yne-1,4-diol comprises nosylate protecting groups.

4. The method of claim 1, wherein the contacting occurs at ambient temperature and ambient pressure.

5. The method of claim 1, wherein the contacting occurs in the presence of a base.

6. The method of claim 5, wherein the base comprises $Cs_2CO_3$.

7. The method of claim 1, wherein the contacting occurs in the presence of $Cs_2CO_3$, $CH_3CN$, dimethyl formamide, or a combination thereof.

8. The method of claim 1, wherein the cyclodecyne is an (R)-cyclodecyne.

9. The method of claim 1, wherein the cyclodecyne is an (S)-cyclodecyne.

* * * * *